United States Patent [19]

McElligott

[11] Patent Number: 4,704,486
[45] Date of Patent: Nov. 3, 1987

[54] HYDROHALOGENATION OF MYRCENE IN THE PRESENCE OF ALCOHOLS

[75] Inventor: Lois T. McElligott, Abington, Pa.
[73] Assignee: Union Camp Corporation, Wayne, N.J.
[21] Appl. No.: 749,924
[22] Filed: Jun. 28, 1985

Related U.S. Application Data

[63] Continuation-in-part of Ser. No. 560,140, Dec. 12, 1983, abandoned.

[51] Int. Cl.[4] ............................................. C07C 17/08
[52] U.S. Cl. .................................. 570/231; 570/236
[58] Field of Search ..................... 570/231, 236, 249

[56] References Cited

U.S. PATENT DOCUMENTS

| 2,123,504 | 7/1938 | Dykstra | 570/236 |
| 2,376,396 | 5/1945 | Soday | 570/231 |
| 2,609,388 | 9/1952 | Knapp et al. | 570/231 |
| 2,871,271 | 1/1959 | Booth | 570/231 |
| 3,055,954 | 9/1962 | Montagna et al. | 570/231 |
| 3,400,162 | 9/1968 | Beets et al. | 570/231 |
| 4,214,098 | 7/1980 | deJong et al. | 570/231 |

FOREIGN PATENT DOCUMENTS

| 160206 | 12/1975 | Japan | 570/236 |
| 919321 | 2/1963 | United Kingdom | 570/231 |

*Primary Examiner*—J. E. Evans
*Assistant Examiner*—Joseph A. Boska
*Attorney, Agent, or Firm*—Kane, Dalsimer, Sullivan, Kurucz, Levy, Eisele and Richard

[57] ABSTRACT

The disclosure is of an improved process for the hydrohalogenation of myrcene in the presence of a catalyst, which comprises carrying out the hydrohalogenation in the presence of an alcohol.

9 Claims, 1 Drawing Figure

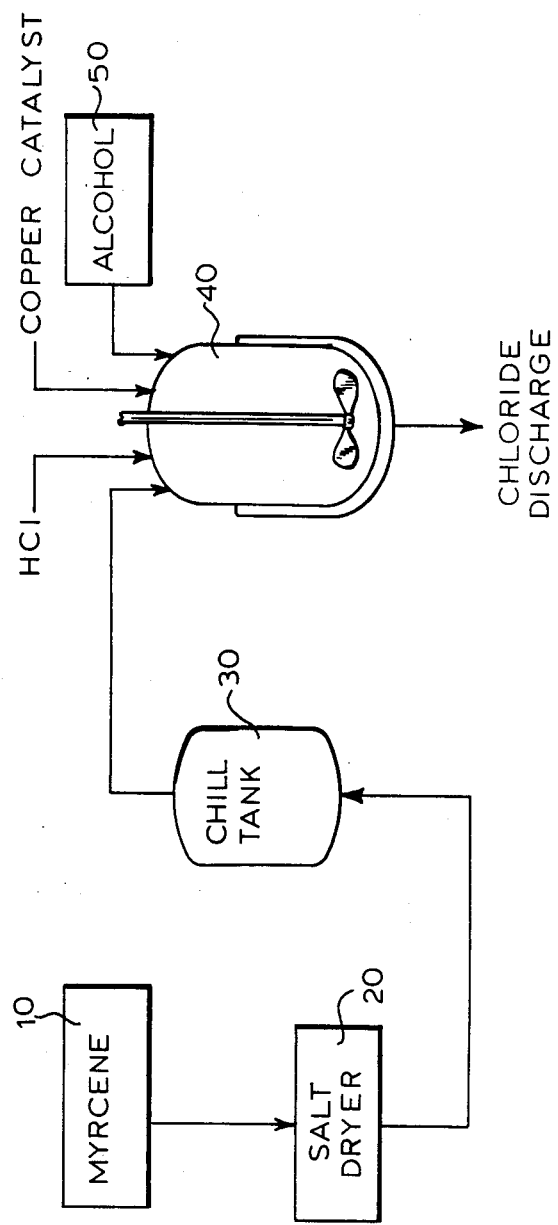

HYDROHALOGENATION OF MYRCENE IN THE PRESENCE OF ALCOHOLS

BACKGROUND OF THE INVENTION

Cross-Reference to Related Application

This application a continuation-in-part of copending U.S. patent application Ser. No. 560,140 filed Dec. 12, 1983, now abandoned.

FIELD OF THE INVENTION

The invention related to processes for the hydrohalogenation of myrcene.

BRIEF DESCRIPTION OF THE PRIOR ART

The literature is replete with descriptions of processes for the hydrohalogenation of conjugated dienes. Representative of such descriptions are those found in the U.S. Pat. Nos. 2,882,323 and 3,016,408 and in British Patent No. 896,262; see also German Offenlegungsschrift No. 1,768,544. The present invention is an improvement over the prior art processes in that it may be carried out in liquid phases of the reactants, at low temperatures and with minimal solvolysis of products. Also, the process of the invention employs relatively inexpensive catalysts which are recoverably and reusable a plurality of times.

The present invention is advantageous when used to hydrochlorinate myrcene. Myrcene is a conjugated diene of the formula:

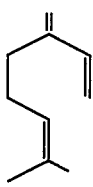

(I)

Upon un-catalyzed hydrochlorination of myrcene the major product is myrcenyl chloride. However, the commercially valuable products of myrcene hydrochlorination are the associated co-products, namely, geranyl chloride and neryl chloride. Hydrochlorination in the presence of a copper catalyst shifts the reaction in favor of the desired co-products. It has been postulated that the hydrochlorination of myrcene in the presence of a copper catalyst proceeds according to the reaction scheme:

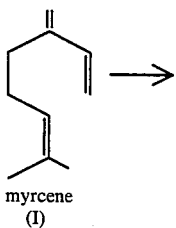

myrcene
(I)

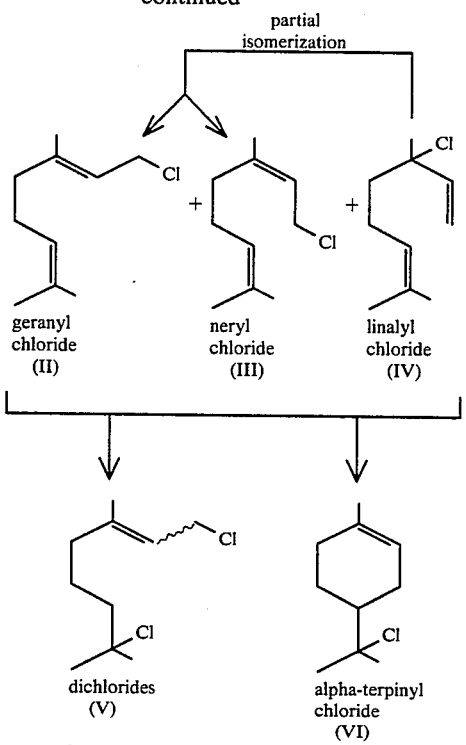

Cyclization may also undesirably occur to form the alpha-terpinyl chlorides.

When the copper catalyst employed is in the form of cupric chloride ($CuCl_2$) the products generally include substantial proportions of linalyl chloride and lesser proportions of the desired geranyl and neryl chlorides. When the copper catalyst is in the form of cuprous chloride, the linalyl chloride product is lessened due, apparently, to partial isomerization to the desired geranyl and neryl chlorides.

From the above proposed reaction scheme, it will be appreciated that any process for hydrochlorination of myrcene, to be commercially feasible, must result in a favorable yield of the desired geranyl (II) and neryl (III) monochlorides and minimal formation of linalyl (IV) and alpha-terpinyl (VI) monochlorides. It was previously appreciated that the relative proportions of monochlorides (II), (III) and (IV) in the hydrochlorination product reaction mixture could be controlled to some degree by selection of the reaction temperature, gas flowrate and catalyst concentration.

We have now found that when the prior art hydrohalogenation of myrcene is carried out in the presence of a catalytic amount of a primary or secondary alcohol containing three or more carbon atoms, then the isomerization of linalyl chloride during the hydrohalogenation reaction is shifted to favor formation of the less-substituted allylic chloride, being geranyl chloride (II) and neryl chloride (III). Use of simpler alcohols, for example methanol, as taught in U.S. Pat. No. 2,376,396 for hydrochlorination of isoprene, does not improve the yield of neryl and geranyl chlorides.

SUMMARY OF THE INVENTION

The invention comprises, a novel method for the hydrohalogenation of myrcene comprising hydrohalogenating myrcene under anhydrous, liquid phase conditions in the presence of a copper-containing hydrohalogenation catalyst, and further comprising carrying out the hydrohalogenation at a temperature below 25° C. in the presence of a catalytic proportion of a primary or secondary alcohol containing at least three carbon atoms.

The improved process of the invention may be carried out in a batch or a continuous manner.

BRIEF DESCRIPTION OF THE DRAWING

The drawing is a schematic representation of a preferred embodiment method of the invention.

DETAILED DESCRIPTION OF THE PREFERRED EMBODIMENTS OF THE INVENTION

The method of the invention is employed advantageously for the hydrohalogenation of myrcene to obtain the geranyl and neryl halides which are intermediates for the manufacture of commercially valuable geraniol and nerol. The improved method of the invention will increase the overall yield of the geranyl and neryl halides over the prior art processes and will improve selectivity of the ratio of geranyl isomer to the neryl isomer. Commercially available myrcene made by pyrolysis of beta-pinene, purified forms of myrcene, and myrcene isolated from natural materials may be provided as the starting material in the preferred process of the invention.

The accompanying drawing is a schematic representation of a preferred embodiment method of the invention for the hydrochlorination of myrcene. As shown in the FIGURE the provided myrcene initially held in tank 10 may be first dried in a conventional salt bed dryer 20 to remove water, as necessary. The dried myrcene is then preferably cooled to a temperature in the range of from about −30° C. to about 25° C.; most preferably circa 10° C. in a cooling unit 30. Alternatively, the myrcene may be cooled first and then processed through a salt bed dryer 20 to remove water. Cooling the starting myrcene prior to drying in the salt bed dryer 20 is somewhat advantageous in that precooling increases drying efficiency in the salt bed dryer 20.

As shown in the FIGURE the dried and cooled myrcene starting material may be passed into a hydrohalogenation apparatus which comprises in the preferred embodiment a stirred tank reactor 40. In reactor 40, hydrohalogenation of the introduced myrcene is carried out in the presence of a catalytic proportion of a hydrohalogenation catalyst, at a temperature within the range of from about −30° C. to about 25° C.; preferably at a temperature within the range of from −10° C. to 20° C., most preferably about 10° C. Hydrohalogenation may be effected, for example, by reaction of the myrcene with a hydrogen halide like hydrogen chloride or hydrogen bromide, in substantially anhydrous form and under substantially anhydrous conditions, i.e. having less than about 5% water present in the reaction mixture. As shown in the FIGURE, the preferred hydrohalogenation is with gaseous hydrogen chloride which is introduced as a gas, possibly generated in a vaporizer, and then metered into the reactor 40 via appropriate conduits Advantageously, the hydrogen chloride is metered into the reactor 40 at a rate of from about 2.0 to about 300 gms/hour/mole of myrcene present in the reactor 40. Preferably, the rate is from about 4.0 to 8.0 gms/hour/mole of myrcene.

The alcohol is introduced into the reactor 40 from storage vessel 50. Myrcene, alcohol, hydrogen chloride and copper catalyst are introduced into the reactor 40 sequentially. Preferably, the reactor 40 after purging with an inert gas such as nitrogen is first charged with the cool myrcene, the copper catalyst, and the alcohol. While cooling and stirring, the hydrogen chloride is added incrementally to the charge.

A wide variety of catalysts for hydrohalogenation of myrcene are well known and include, for example, any copper compound having a valency of 2 or less, including metallic copper. Any copper compound convertible to the halide such as the bromide, iodide or chloride under conditions of the reaction may also be used. Representative of copper catalysts advantageously employed are the chloride, bromide, carbonate, oxide, acetate, formate, sulfate, and like derivative cupric and cuprous compounds. Preferred as the hydrochlorination catalyst in the improved process of the invention is cuprous chloride. Catalytic proportions of the anhydrous hydrohalogenation catalyst are generally within the weight range of from about 0.01 to 10 percent of the dry myrcene, preferably about 0.5 percent.

A wide range of primary and secondary alcohols may be employed in the improved process of the invention. Advantageously the alcohol selected is one which is a fluid under the process conditions and inert to reaction with the reaction mixture ingredients. Representative of such alcohols are hexanol, decanol, isopropanol, isobutanol, 3-pentanol, decanol, cyclohexanol, and the like. Preferred alcohols are those of the formula:

$$R\text{—}OH \qquad (VII)$$

wherein R represents alkyl or aralkyl.

The term "alkyl" as used herein means the monovalent moiety obtained upon removal of a hydrogen atom from a parent alkane. Representative of alkyl are alkyl of 3 to 25 carbon atoms, inclusive, such as propyl, butyl, pentyl, hexyl, heptyl, octyl, nonyl, undecyl, decyl, dodecyl, octadecyl, nonodecyl, eicosyl, heneicosyl, docosyl, tricosyl, tetracosyl, pentacosyl and the isomer forms thereof. The term "aralkyl" as used herein means alkyl as defined above wherein a hydrogen atom has been replaced with a monovalent moiety obtained upon removal of a hydrogen atom from an aromatic hydrocarbon. Representative of aralkyl are aralkyl of 7 to 25 carbon atoms, inclusive, such as benzyl, phenethyl, phenpropyl, phenbutyl, phenhexyl, napthocotyl and the like.

Preferably, the R moiety will contain from 3 to 10 carbon atoms, inclusive.

It will be appreciated that under specific conditions of operating the process of the invention, certain of the above described alcohols of the formula (VII) given above have advantages over other compounds of the same general formula. Selection of a particular alcohol (VII) for use under specific process conditions, for optimum yields may be made by trial and error technique.

The alcohol is used in a proportion to isomerize, during the hydrohalogenation reaction, at least some of the linalyl chloride produced in the method of the invention. Such a proportion is generally within the range of from about 0.01 to 10 percent by weight of the myrcene charge, preferably 0.1 to 5 percent. This proportion of alcohol catalyst is added to the hydrohalogenation reaction mixture, without consideration of any alcohol by-product which may have been undesirably formed in the reaction mixture by solvolysis of desired product. Optimum proportions will depend to some extent upon the alcohol selected and may be determined by trial and error technique.

The controlling reaction rate in the hydrohalogenation process of the invention is the isomerization of the linalyl halide to the desired geranyl/neryl halides. This is controlled by residence time in the hydrohalogenation reaction zone. We have found that in the hydrochlorination of myrcene, the preferred minimum total residence time is within the range of from 3 to 15 hours, and most preferably 5 to 8 hours under the above-described operating temperatures. The presence of linalyl chloride in the reaction mixture may be monitored by conventional analytical techniques. Longer residence times in the hydrochlorination reactor may cause a yield loss due to conversion of the monochlorides to alpha-terpinyl chloride. Shorter residence times may not be sufficient to isomerize the linalyl chloride to the desired geranyl/neryl chlorides.

When it has been determined that hydrohalogenation has occurred to a maximum desired point, the hydrohalogenation product mixture is passed from the hydrohalogenation apparatus. The alcohol may be recovered by distillation and reused a plurality of times.

The following examples describe the manner and process of making and using the invention and set forth the best mode contemplated by the inventors of carrying out the invention but are not to be construed as limiting. All parts given are by weight unless otherwise indicated.

EXAMPLES

Examples 1-8

To a 1 liter reaction vessel is charged 300.0 g myrcene (70 wt%), 1.0 g cuprous chloride and an alcohol as described in Table 1 below. The mixture is purged with nitrogen and cooled to 0° C. Hydrogen chloride gas was added at a rate of 7-8 g/hour while maintaining the temperature at 10° C. At the end of the reaction (7 hours), monitored by infrared spectroscopy to a 1% myrcene level, the reaction product is neutralized with sodium carbonate and aqueous sodium hydroxide. The product was analyzed by gas chromatography. The results are shown in Table 1. Linalyl, neryl and geranyl chlorides are abbreviated LCl, NCl, and GCl respectively in the Table 1.

TABLE 1

| Example No. | Alcohol and Amount Used | Molar Yield of Products % LCl | NCl + GCl | CGl:NCl Ratio |
|---|---|---|---|---|
| 1 | None (control) | 18 | 69 | 1.26 |
| 2 | Isobutanol, 0.7 g | 8 | 79 | 1.59 |
| 3 | Isopropanol, 0.6 g | 7 | 79 | 1.60 |
| 4 | Hexanol, 1.0 g | 10 | 76 | 1.23 |
| 5 | Cyclohexanol, 1.0 g | 12 | 76 | 1.17 |
| 6 | 3-Pentanol, 0.9 g | 9 | 76 | 1.24 |
| 7 | Geraniol 1.5 g | 10 | 73 | 1.21 |
| 8 | n-Decanol, 1.5 g | 9 | 77 | 1.30 |

What is claimed:

1. In a method for the hydrohalogenation of myrcene to obtain the linalyl, geranyl and neryl halide isomers, which comprises; hydrohalogenating dry mrycene under anhydrous, liquid phase conditions in the presence of a catalytic proportion of a copper-containing hydrohalogenation catalyst at a temperature below 25° C. the improvement which comprises; the further presence of a catalytic proportion of an isomerization catalyst which is an alcohol selected from the group consisting of a primary and a secondary alcohol containing at least three carbon atoms; whereby there is obtained linalyl, geranyl and neryl halides with a shift favoring formation of the geranyl/neryl halides over the linalyl halide.

2. The process of claim 1 wherein the alcohol is selected from the group of the formula:

R—OH wherein R is selected from the group consisting of alkyl having 3 to 25 carbon atoms, inclusive and aralkyl having 7 to 25 carbon atoms, inclusive.

3. The process of claim 1 wherein the hydrohalogenation temperature from about −10° C. to about 20° C.

4. The process of claim 1 wherein the hydrohalogenation catalyst is cuprous chloride.

5. The process of claim 4 wherein the catalytic proportion of copper catalyst is within the weight range of about 0.01 to about 10.0 percent of the dry myrcene.

6. The process of claim 1 wherein the hydrohalogenation is carried out for a period of from about 3 to 15 hours.

7. The process of claim 1 wherein the molar ratio of alcohol to copper catalyst is within the range of from about 0.1 to about 5.0.

8. The process of claim 2 wherein the alcohol is selected from the group consisting of isopropanol, isobutanol, hexaol, cyclohexanol, 3-pentanol, octanol, decanol and geraniol.

9. The process of claim 1 wherein the catalytic proportion of the isomerization catalyst is within the range of from about 0.01 to 10 percent by weight of the dry myrcene.

* * * * *